(12) United States Patent
Amano

(10) Patent No.: US 7,771,988 B2
(45) Date of Patent: Aug. 10, 2010

(54) CONTROL DEVICE FOR FERMENTER

(75) Inventor: Ken Amano, Hitachiota (JP)

(73) Assignee: Hitachi, Ltd., Tokyo (JP)

( * ) Notice: Subject to any disclaimer, the term of this patent is extended or adjusted under 35 U.S.C. 154(b) by 591 days.

(21) Appl. No.: 11/355,954

(22) Filed: Feb. 17, 2006

(65) Prior Publication Data

US 2006/0216818 A1   Sep. 28, 2006

(30) Foreign Application Priority Data

Mar. 24, 2005   (JP) .............................. 2005-086415

(51) Int. Cl.
*C12M 1/34* (2006.01)
(52) U.S. Cl. .................................. 435/287.5; 700/266
(58) Field of Classification Search .............. 435/287.5; 700/266; 702/19
See application file for complete search history.

(56) References Cited

U.S. PATENT DOCUMENTS 4,064,015 A * 12/1977 Nyiri et al. ...................... 435/3
2003/0085892 A1 * 5/2003 Mashimo ..................... 345/420

FOREIGN PATENT DOCUMENTS

| JP | 06-153909 | 6/1994 |
| JP | 07-313190 | 12/1995 |
| JP | 2001-075947 | 3/2001 |
| JP | 2001-231544 | 8/2001 |

OTHER PUBLICATIONS

Langheinrich et al, "Oxygen Transfer in Stirred Bioreactors under Animal Cell Culture Conditions", Trans IChemE, vol. 80, Patt C, Mar. 2002, pp. 39-44.

Hristov, H.V, et a., "A Simplified CFD for Three-Dimensional Analysis of Fluid Mixing, Mass Transfer and BioReaction in a Fermenter Equipped with Tripple Novel Geometry Impellers", TransIChemE, Part C, Food & Bioproducts Processing, 2004, 82(C1), pp. 22-34 (with English translation).

Umino, H., et al, "Bioprocess Engineering: Measurement and Control", Bioengineering Text Series, Jan. 20, 1997, pp. 1-52 (with partial English translation).

Ishizaki, A., "Behavior of Carbon Dioxide and Its Function Affected to the Fermentation in Submerged Culture", Hakkokogaku, vol. 65, No. 1, 1987, pp. 59-69 (with English Abstract and partial English translation).

Djebbar, R., et al, "Numerical Computation of Turbulent Gas-Liquid Dispersion in Mechanically Agitated Vessels", Trans IChemE, vol. 74, Part A, May 1996, pp. 492-498.

* cited by examiner

*Primary Examiner*—William H Beisner
*Assistant Examiner*—Michael Hobbs
(74) *Attorney, Agent, or Firm*—Mattingly & Malur, P.C.

(57) ABSTRACT

The control device according to the present invention includes an input device for entering measured data from a measurement unit, which measures nutrient components, the concentrations of oxygen, carbon dioxide, and biomass in a culture medium; a processor for calculating nutrient components uptake rate, oxygen uptake rate and carbon dioxide exhaust rate per unit amount of biomass from the measured data entered in the aforementioned input device, as well as volumetric mass transfer coefficient kLa from turbulent energy k and a turbulent energy dissipation rate e, both of which are calculated by a transport equation, as well as a diffusion coefficient D, followed by calculating the concentrations of the nutrient components, dissolved oxygen and dissolved carbon dioxide in any area in the fermenter; and a display for displaying concentration distribution of the nutrient components, dissolved oxygen, and dissolved carbon dioxide in the fermenter.

12 Claims, 9 Drawing Sheets

(a) Fermenter structure display    (b) Computed fermenter grid display

Fig.1(b) Time-integration algorithm for processor

Fig. 4-1
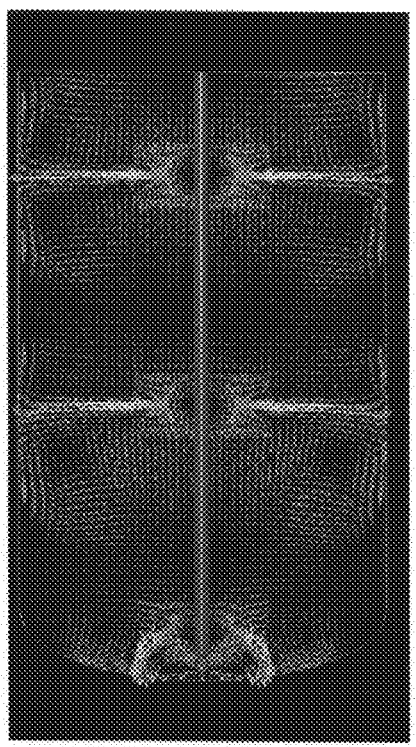
(a) Flow rate vector display
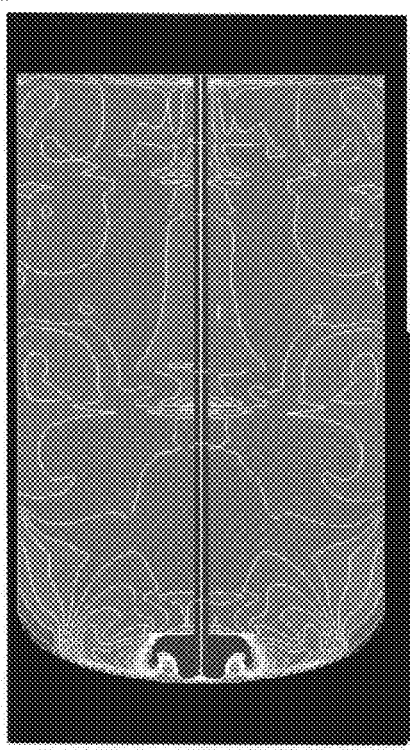
(b) Gas holdup ratio display
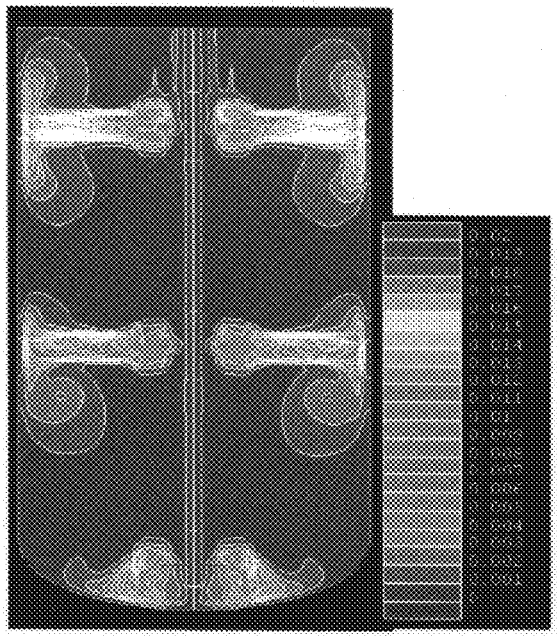
(c) Distribution display of turbulent energy k
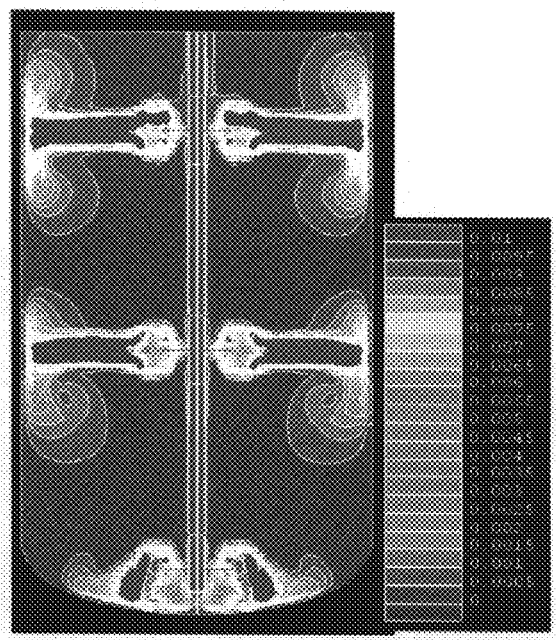
(d) Distribution display of turbulent energy dissipation rate ε

Fig. 4-2
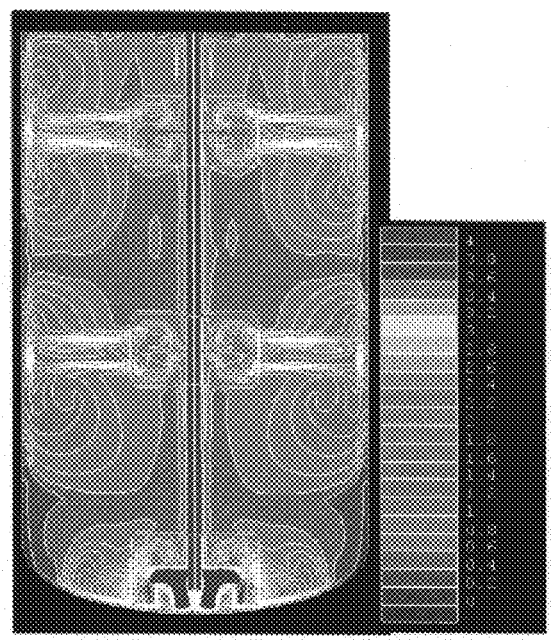
(e) Distribution display of volumetric
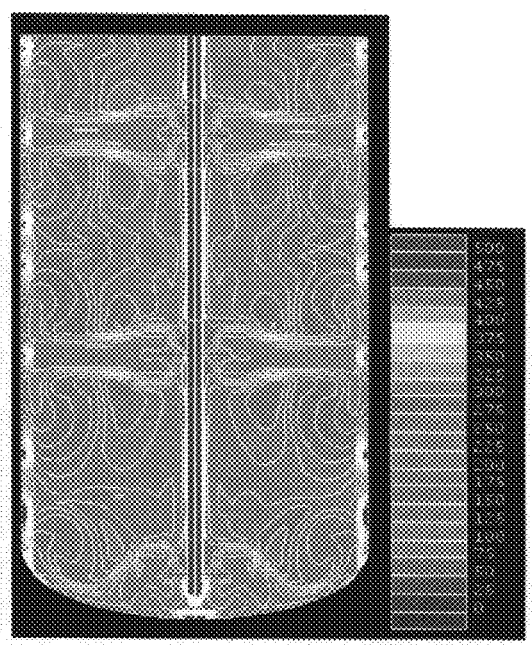
(f) Distribution display of Kolmogorov scale
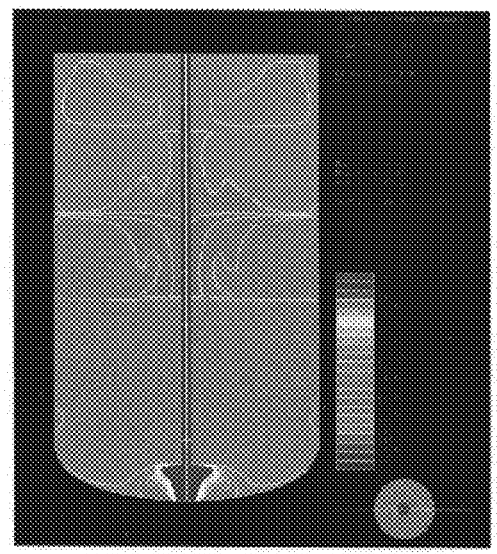
(g) Distribution display of oxygen concentration, DO(%air.sat)
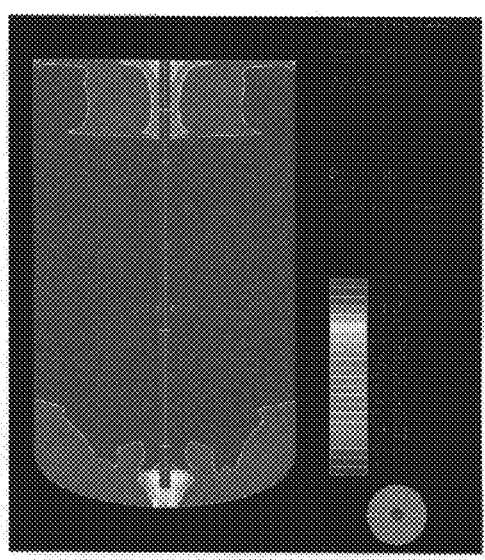
(h) Distribution display of carbon dioxide concentration, CO2(mmHg)

(a) Dependencies of turbulent energy k and turbulent energy dissipation ε on rotation speed (b) Dependency of volumetric oxygen transfer coefficient Kla on rotation speed

CONTROL DEVICE FOR FERMENTER

FIELD OF THE INVENTION

The present invention relates to a control device controlling a fermenter for culturing biomass such as mammalian cells or microorganisms.

BACKGROUND OF THE INVENTION

In an industrial culture, oxygen necessary for biomass to grow in a culture medium containing nutrient components such as glucose and glutamine is supplied in a form of a bubble aerating gas or supplied by aeration onto a liquid free surface while the culture medium is often frequently stirred to grow the biomass, harvesting a responsible material produced by the biomass. To successfully achieve biomass culture, it is required that inner fermenter conditions suitable for biomass culture be secured. In contrast, the structure and running conditions of the fermenter contribute to deviation from these suitable inner fermenter conditions.

To ensure an increased volumetric mass transfer coefficient kLa for oxygen in the fermenter, and homogeneous mixture of the nutrient components and a dissolved oxygen concentration, the culture medium is stirred by impellers. Is difficult to achieve high kLa and sufficient homogeneity as for high-viscosity culture media. Though an attempt has been made to experimentally obtain the volumetric oxygen transfer coefficient kLa for each type of fermenter, in such an experimental method (Japanese Patent Publication (Kokai) No. 2001-231544), kLa varies with the tank diameter of the fermenter, the diameter of bubbles, the diameter of impellers, and the rotation speed and consistently depends on the type of fermenter. Therefore, this method lacks generality. In the case where aeration onto the liquid free surface and aerating into the culture medium are combined, the ratio between both two depends on the conditions, making it difficult to obtain general knowledge. To enhance an increase in kLa and the homogeneity, the rotation speed of the impellers may be increased, though usually, agitation power constraints it. In culturing the mammalian cells, such a problem arise that to strong agitation may bring the cells to death. To avoid experimental constraints, an attempt has been made to use fluid numeric simulation in designing the fermenter structure (Japanese Patent Publication (Kokai) No. 2001-75947), which has provided no knowledge of a fluid field suitable for biomass growth. No method for applying fluid numeric simulation to control has been established.

Any starvation of nutrient components in the culture process inhibits growth of the biomass. In many cases, the components such a lactate, ammonia, and alcohol produced as by-products suppress the growth of the biomass, deteriorating the yield of responsible products. Accordingly, it is always important to measure the components in the culture medium and to sustain the nutrient components during fermenter's running. However, no satisfactory technique has been established for reflecting the measurement results in fermenter control. An attempt has been made to make a model of a biomass growing process by a differential equation of reaction dynamics, though no computer-aided control method, which combines both the techniques for modeling of the biomass growing process and achieving of hydrodynamic conditions in the fermenter, has been reported.

SUMMARY OF THE INVENTION

To solve these problems, an object of the present invention is to provide the control device for fermenter, which is capable of producing the biomass and/or components produced by the biomass at a high yield by applying the fluid numerical simulation technique to reasonably find the running conditions suitable for the fermenter.

The present invention, which has attained the abovementioned object, is composed of a plurality of the following means.

The control device for fermenter according to the present invention comprises; an input means connected to the fermenter, in which biomass is cultured while oxygen gas is being blown into a culture medium and the culture medium is being stirred, for entering measured data output from a measurement means for measuring nutrient components, concentration of oxygen, concentration of carbon dioxide, and concentration of biomass in a medium; a computation means for calculating nutrient components uptake rate, oxygen uptake rate and carbon dioxide exhaust rate per unit amount of biomass from the measured data entered at the aforementioned input means, as well as volumetric mass transfer coefficient kLa from turbulent energy k and a turbulent energy dissipation rate e, both of which are calculated by a transport equation, as well as a diffusion coefficient D, followed by calculating the concentrations of the nutrient components, dissolved oxygen, and dissolved carbon dioxide in any area in the fermenter using an algorithm to numerically integrate a differential equation describing variations in medium components over time from the calculated nutrient components uptake rate, the calculated oxygen uptake rate, the calculated carbon dioxide exhaust rate, and the calculated volumetric mass transfer coefficient kLa; and a display means for displaying concentration distributions of the nutrient components, dissolved oxygen, and dissolved carbon dioxide in the fermenter based on the concentrations of the nutrient components, dissolved oxygen, and carbon dioxide in any area of the fermenter calculated at aforementioned computation means.

According to the present invention, the variations of medium components over time and spatial distributions of the nutrient components in the fermenter are calculated by combining the differential equation describing the medium components with equations of fluid dynamics for numerical, discrete, and algebraic evaluation. This gives information on how the biomass grows in the any region in the fermenter and on what kind of fluid field is suitable for biomass growth. Moreover, the present invention provides the volumetric mass transfer coefficient kLa as a function $k_L a$ ($k$, $\epsilon$, D) among $k$, $\epsilon$, and the diffusion coefficient D based on the result of an experimental study on the relationship among a mass transfer coefficient for a turbulent field, and turbulent energy k and turbulent energy dissipation rate $\epsilon$. This allows the volumetric mass transfer coefficient $k_L a$ for the any region in the fermenter of any structure to be calculated based only on the properties of the turbulent field and the values for gas properties without depending on the structure of the fermenter. Therefore, the concentrations of the aforementioned medium components, as well as of oxygen, carbon dioxide, and so on, can be calculated in the any point in the fermenter. Also, the structure of the fermenter suitable for biomass growth can be determined. Further, the present invention provides the nutrient supply algorithm based on time differential equations for the medium components by means of dynamic programming.

The control device for the fermenter and a fermentation unit according to the present invention can display the distributions of dissolved oxygen concentration and dissolved carbon dioxide concentration on its display screen to facilitate the determination of conditions suitable for biomass growth in the fermenter.

BRIEF DESCRIPTION OF THE DRAWINGS

FIG. 2A and FIG. 2B show mesh data on the inside of the fermenter generated by a mesh data generator.

FIGS. 4-1A, 4-1B, 4-1C, and 4-1D show an example of the results of computations indicated on a display, in which FIG. 4-1A is an example of the displayed flow rate vector; FIG. 4-1B is an example of the displayed gas holdup ratio, FIG. 4-1C is an example of the displayed distribution of turbulent energy k, and FIG. 4-1D is an example of the displayed distribution of turbulent energy dissipation rate $\epsilon$.

FIGS. 4-2E, 4-2F, 4-2G, and 4-2H show an example of the results of computations indicated on the display; in which FIG. 4-2E is an example of the displayed distribution of volumetric oxygen transfer coefficient KLa, FIG. 4-2F is an example of the displayed distribution of Kolmogorov scale, FIG. 4-2G is an example of the displayed image of the oxygen concentration distribution, and FIG. 4-2H is an example of the displayed image of the carbon dioxide concentration distribution.

FIG. 5A and FIG. 5B show an example of a graph of the result of computations indicated on the display; in which FIG. 5A is an example of the displayed graph of the relationship between the rotation speed of impellers; and the turbulent energy k and the turbulent energy dissipation rate $\epsilon$, and FIG. 5B is an example of a graph of the relationship between the rotation speed of the impellers; and the total volumetric oxygen transfer coefficient Kla, the volumetric liquid-surface oxygen transfer coefficient Kla,s, and the volumetric bubble-oxygen transfer coefficient Kla,b.

DETAILED DESCRIPTION OF THE PREFERRED EMBODIMENTS

Figure 1:
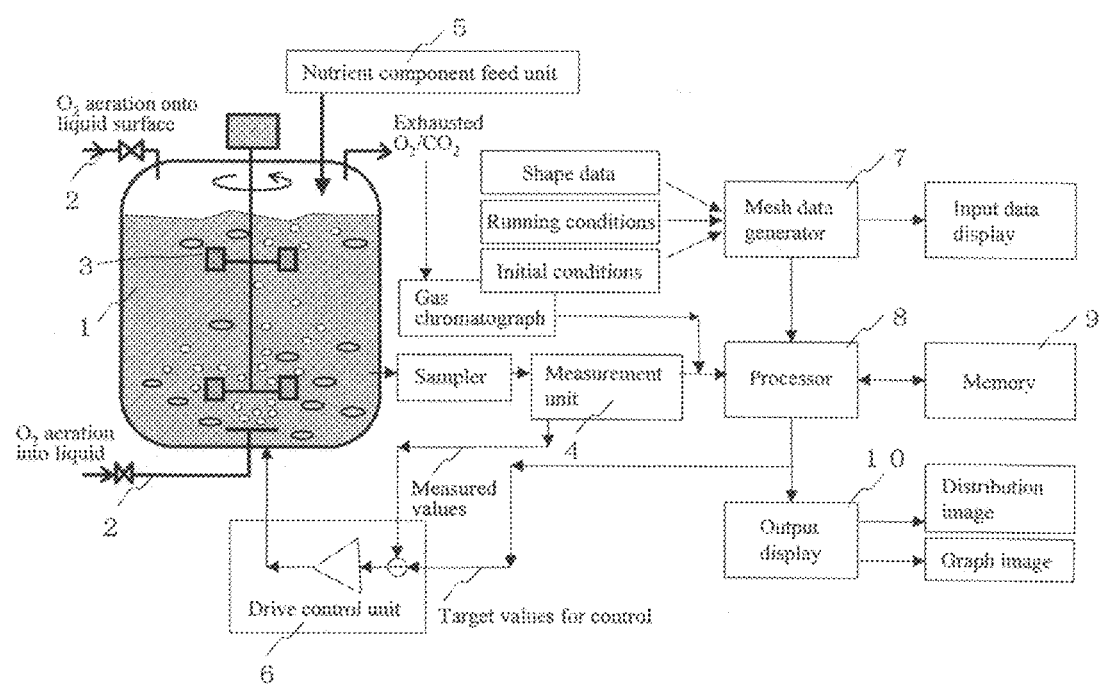
FIG. 1 is a block diagram showing the structures of a control device for fermenter and a fermenter unit according to the present invention.

Now, by reference to the drawings, the control device for fermenter according to the present invention is described in detail. As shown in FIG. 1, the control device for fermenter according to the present invention controls the fermentation unit having a fermenter 1, which cultures the biomass under given conditions. The fermentation unit comprises the fermenter 1, a aerating unit 2, which supplies a oxygen gas into the fermenter 1, impellers 3, which stire the culture medium in the fermenter 1, a measurement unit 4, which measures the concentrations of oxygen, nutrients, biomass, or the like in the culture medium, a nutrient component feed unit 5, which supplies the nutrient components in the culture medium, and a drive control unit 6, which supplies drive control signals to the aerating unit 2, the impellers 3, and the nutrient component feed unit 5 in the fermenter 1.

As shown in FIG. 1, the control device according to the present invention comprises a mesh data generator 7, which generates mesh data for the fermenter 1 based on shape data on the fermenter 1, a processor 8, which executes computations in accordance with a running control program, memory 9, which stores the running control program, and an output display 10, which indicates the results of computations executed at the processor 8. The control device according to the present invention can be specifically implemented using hardware resources comprising an interface for entering data output from the measurement unit 4 of the fermenter 1, an input device for entering the shape data on the fermenter 1, or the like, the computation means such as a CPU, a memory means such as hard disk, nonvolatile memory, and volatile memory, and an displaying means such as a display. Alternatively, the control device according to the present invention may be implemented as an integrated type, which has been integrated in the fermenter unit. This means that the present invention may implement the fermentation unit having the control device for fermenter.

The drive control unit 6, which is incorporated a PID (Proportional Integral Differential) control system, outputs the control signals based on target control values calculated by the processor 8 using, for example measured values input from the measurement unit 4 via the interface.

The measurement unit 4 may measure, for example the concentration of the biomass contained in the culture medium sampled by a sampler, the components having positive effects on cell growth, and the components having negative effects on cell growth and also measure the concentrations of dissolved oxygen and dissolved carbon dioxide contained in the culture medium by a chromatographic system. The term "the components having positive effects on cell growth" described herein includes the nutrient components such as glucose and glutamic acid. The term "the components having negative effects on cell growth" described herein includes substances such as lactate and carbon dioxide produced in the culture process.

The mesh data generator 7 enters data to be calculated by means of the input means so as to generate mesh data, and sends it to the processor 8. The term "the input data" described herein are the shape data such as the diameter and the height of the fermenter, the diameter width, and number of impellers of the fermenter; conditions such as an impeller rotation speed and a sparger gas flow rate; and initial values data such as the initial concentrations of culture medium components and biomass. The mesh data generated here may be output to the input data display unit, enabling the target to be analyzed to be checked as shown in FIGS. 2A and 2B.

Figure 3:
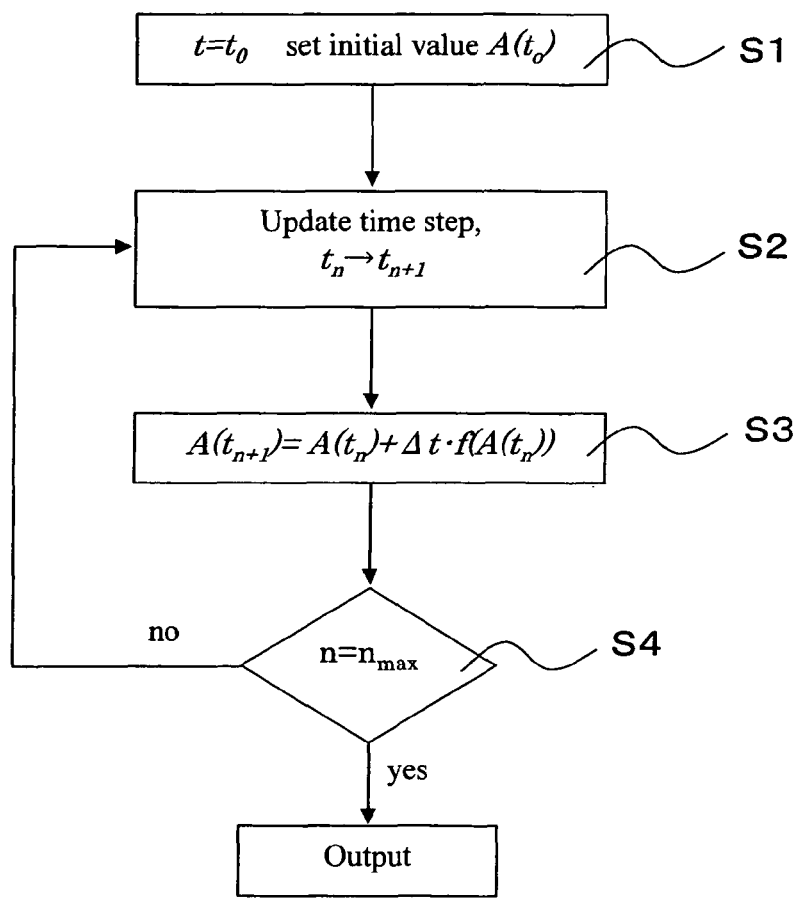
FIG. 3 is a flowchart explaining an algorithm for sequentially, numerically, discretely, and algebraically integrating the differential equations for time.

The processor 8 executes computations in accordance with the program stored in the memory 9. As shown in FIG. 3, the program comprises the algorithm, which numerically, discretely, and algebraically integrates the time differential equation. In other words, the program comprises a step 1, at which t is initialized to $t_0$; a step 2, at which a time step is updated to $t_{n+1}$; a step 3, at which $A(t_{n+1})=A(t_n)+\Delta t \cdot f(A(t_n))$ is calculated; and a step 4, at which $n=n_{max}$ is determined.

Here, the differential equation n to be integrated at the processor 8 herein is an equation of motion (Navie-Stokes equation) for a flow rate of flow $u_f$(m/s), which may be represented by:

[Formula 1]

$$\frac{\partial \vec{u}_f}{\partial t} + (\vec{u}_f \cdot \nabla)\vec{u}_f = -\frac{1}{\rho}\nabla P + \nabla \cdot (v_t \nabla \vec{u}_f) + \rho \vec{g} \quad (1)$$

In the formula (1), $\rho$ is the density (kg/m³) of a fluid, P is pressure (Pa), g is acceleration for gravity (m/s²), and $v_t$ is an eddy viscosity coefficient (m²/s).

The differential equations integrated at the processor 8 are the transport equation of turbulent energy k(m²/s²) represented by:

[Formula 2]

$$\frac{\partial k}{\partial t} + (\vec{u}_f \cdot \nabla)k = \nabla \cdot (v_t \nabla k) + P_k - \varepsilon \quad (2)$$

and the transport equation for the turbulent energy dissipation rate $\varepsilon$ (m²/s³) represented by:

[Formula 3]

$$\frac{\partial \varepsilon}{\partial t} + (\vec{u}_f \cdot \nabla)\varepsilon = \nabla \cdot (v_t \nabla \varepsilon) + c_1 \frac{\varepsilon}{k} P_k - c_2 \frac{\varepsilon^2}{k}, \quad (3)$$
$$C_1 = 1.44$$
$$C_2 = 1.92$$

A turbulent energy production term $P_K$(m²/s³) is calculated by the following formula (4):

[Formula 4]

$$P_k = \sum_{i=1}^{3}\sum_{j=1}^{3} \frac{1}{2} v_t \left(\frac{\partial \overline{u}_i}{\partial x_j} + \frac{\partial \overline{u}_j}{\partial x_i}\right)^2 \quad (4)$$

The eddy dynamic viscosity $v_t$ is calculated by the following formula (5):

[Formula 5]

$$v_t = c_\mu \frac{k^2}{\varepsilon}, \quad C_\mu = 0.09 \quad (5)$$

It should be noted that in formulae (4) and (5), $C_1$, $C_2$, and $C_\mu$ are model constants of a turbulent model.

A gas holdup ratio $\alpha_b$ in the culture medium is calculated by:

[Formula 6]

$$\frac{\partial \alpha_b}{\partial t} + (\vec{u}_g \cdot \nabla)\alpha_b = S_\alpha \quad (6)$$

In the formula (6), bubbles are assumed to move at a flow rate $u_g$(m/s) different from the flow rate of flow $u_f$(m/s). Where, $u_g$ is obtained by:

[Formula 7]

$$\overline{u}_g = \overline{u}_f + \overline{u}_d \quad (7)$$

In the formula (7), $u_d$ is a bubble terminal velocity depending on a bubble diameter, which is often entered in the form of input data or a function formula being set the bubble diameter as a parameter. It should be noted that the flow rate of bubbles $u_g$ may be obtained by the dynamic equation similar to that in the formula (1); however, when the bubbles have any of smaller diameters, it is convenient to use the formula (7). The formulae (1) to (7) may be used to calculate the flow rate and gas holdup distributions in the fermenter.

The transport equation of cell density (Xa)(cells/mL) of the cells transported at a flow rate $u_f$, which is integrated at the processor 8, is represented by:

[Formula 8]

$$\frac{\partial X_a}{\partial t} + (\vec{u}_f \cdot \nabla)X_a - \nabla \cdot (v_t \nabla X_a) = \mu X_a - K_d X_a \quad (8)$$

In the formula (8), $\mu$ is a specific growth rate (1/s) and Kd is a death rate (1/s). The transport equation of the medium component transported at the flow rate $u_f$, for example glucose (Glc) transported at the flow rate $u_f$, which is integrated at the processor 8, is represented by:

[Formula 9]

$$\frac{\partial Glc}{\partial t} + (\vec{u}_f \cdot \nabla)Glc - \nabla \cdot (v_t \nabla Glc) = -q_{Glc} X_a \quad (9)$$

Similarly, the transport equation of the medium component, for example glutamine (Gln) transported at the flow rate $u_f$ is represented by:

[Formula 10]

$$\frac{\partial Gln}{\partial t} + (\vec{u}_f \cdot \nabla)Gln - \nabla \cdot (v_t \nabla Gln) = -q_{Gln} X_a - \kappa_{gln} Gln \quad (10)$$

The transport equation of the medium component, for example lactate (Lac) transported at the flow rate $u_f$ is represented by:

[Formula 11]

$$\frac{\partial Lac}{\partial t} + (\vec{u}_f \cdot \nabla)Lac - \nabla \cdot (v_t \nabla Lac) = q_{Lac} X_a - \kappa_{Lac} Lac \quad (11)$$

The transport equation of the medium component, for example ammonia (Amm) transported at the flow rate $u_f$ is represented by:

[Formula 12]

$$\frac{\partial Amm}{\partial t} + (\vec{u}_f \cdot \nabla)Amm - \nabla \cdot (v_t \nabla Amm) = q_{Amm} X_a + \kappa_{Gln} Gln \quad (12)$$

It should be noted that the medium components are not limited to these substances and the transport equation may be described for any of the biological metabolites involved in mammalian cell culture.

In formulae (8) to (12), the right sides are reaction dynamics model equations, which describe growth, production, and consumption of the cells (formula (8)) and medium components (formulas (9) to (12)) through the process of metabolism. These reaction models are different depending on the type of a stem or cell line to be cultured. The models applicable to the general processes of mammalian cell culture are exemplified by the following formulae.

In the formulae (8) to (12), the reaction equations extracted only for mammalian cells are represented by:

[Formula 13]
$$\frac{dX_a}{dt} = \mu X_a - k_d X_a$$
$$\frac{dGlc}{dt} = -q_{Glc} X_a$$
$$\frac{dGln}{dt} = -q_{Gln} X_a - \kappa_{Gln} Gln$$
$$\frac{dLac}{dt} = q_{Lac} X_a - \kappa_{Lac} Lac$$
$$\frac{dAmm}{dt} = q_{Amm} X_a + \kappa_{Gln} Gln$$

Where,

[Formula 14]
$$\mu = \mu_{max} \frac{Glc}{Glc + K_{Glc}} \cdot \frac{Gln}{Gln + K_{Gln}} \cdot \frac{1}{\left[1 + \frac{Lac^2}{K_{Lac}}\right]} \cdot \frac{1}{\left[1 + \frac{Amm^2}{K_{Amm}}\right]}$$

and $$k_d = k_{d0} e^{-\alpha \mu} \quad \text{[Formula 15]}$$

are defined.

In addition,

[Formula 16]
$$q_{Glc} = \frac{\mu}{Y_{Glc}} + m_{Glc} + q_{E,Glc}^{Glc} \frac{Glc - Glc_0^{Glc}}{(Glc - Glc_0^{Glc}) + K_{Glc}^{Glc}} +$$
$$q_{E,Glc}^{Gln} \frac{Gln - Gln_0^{Glc}}{(Gln - Gln_0^{Gln}) + K_{Gln}^{Glc}}$$
$$q_{Gln} = \frac{\mu}{Y_{Gln}} + m_{Gln} + q_{E,Gln}^{Gln} \frac{Gln - Gln_0^{Gln}}{(Gln - Gln_0^{Gln}) + K_{Gln}^{Gln}}$$
$$q_{Lac} = \frac{\mu}{Y_{Lac}} + m_{Lac} + q_{E,Lac}^{Glc} \frac{Glc}{Glc + K_{Glc}^{Lac}}$$
$$q_{Amm} = \frac{\mu}{Y_{Amm}} + m_{Amm} + q_{E,Amm}^{Glc} \frac{Glc}{Glc + K_{Glc}^{Amm}} + q_{E,Amm}^{Gln} \frac{Gln}{Gln + K_{Gln}^{Amm}}$$

are defined.

The transport equation for the dissolved oxygen calculated at the processor 8 is represented by:

[Formula 17] (13)
$$\frac{\partial D_O}{\partial t} + (\bar{u}_f \cdot \nabla) D_O - \nabla \cdot (v_t \nabla D_O) =$$
$$-q_{O2} X_o + K_{L,O,b} a_b (D_{O,b}^{eq} - D_O) + K_{L,O,s} a_s (D_{O,s}^{eq} - D_O)$$

Similarly, the transport equation for dissolved carbon dioxide calculated at the processor 8 is represented by:

[Formula 18] (14)
$$\frac{\partial D_{CO_2}}{\partial t} + (\bar{u}_f \cdot \nabla) D_{CO_2} - \nabla \cdot (v_t \nabla D_{CO_2}) =$$
$$q_{CO2} X_a + K_{L,CO_2,b} a_b (D_{CO_2,b}^{eq} - D_{CO_2}) + K_{L,CO_2,s} a_s (D_{CO_2,s}^{eq} - D_{CO_2})$$

In both formulae (13) and (14), the left sides indicate a transport term in a flow field and the right sides indicate terms for carbon dioxide production and consumption caused by mass transfer at a gas-liquid interface and metabolism. In the formulae, $q_{o2}$ is the oxygen uptake rate (mg/cell·s) per unit cell and $q_{CO2}$ is a carbon dioxide exhaust rate (mg/cell·s) per unit cell. For mass transfer at the gas-liquid interface, the volumetric mass transfer coefficient $k_L a$ is obtained by multiplying a mass transfer coefficient velocity $K_L$ at the gas-liquid interface and a specific surface area a, which comprises of those at a bubble-liquid interface and at a gas-culture medium interface on the liquid free surface. A subscript b is used for that of the bubble-liquid interface and a subscript S is used for that of the liquid free surface. The specific surface area $a_S$ (1/m) is obtained by dividing a liquid free surface area $S_{surf}$ (m$^2$) by the volume of the fermenter Vol (m$^3$) ($a_S = S_{surf}$/Vol). The specific surface area $a_b$ is obtained by $a_b = 6\alpha/Dp$ using a gas holdup ratio number density $\alpha_b$ and the bubble diameter Dp(m). The gas holdup ratio number density $\alpha_b$ is obtained by the aforementioned formula (6). $S_\alpha$ is bubbles holdup blown from the sparger at an interval of unit time.

In the aforementioned formula, $\mu_{max}, k_{d0}, \alpha, K_i, K_j^i, Y_i, m_i, q_{Ei}^j, \kappa_j (i,j=\text{Glc, Gln, Lac, Amm})$ [Formula 19]

are experimental constants used in the reaction dynamics model, respectively, and $D_{O,b}^{eq}, D_{O,s}^{eq}, D_{CO2,b}^{eq}, D_{cO2,s}^{eq}$ [Formula 20]

are the concentration of dissolved oxygen, which comes to balance a partial pressure of oxygen in the bubbles, the concentration of dissolved oxygen, which comes to balance a partial pressure of oxygen on the liquid surface, the concentration of dissolved carbon dioxide, which comes to balance a partial pressure of carbon dioxide in the bubbles, and the concentration of dissolved carbon dioxide, which comes to balance a partial pressure of carbon dioxide on the liquid surface, respectively. In the formula (13), the oxygen gas in the bubbles and on the liquid free surface dissolves into the liquid under the volumetric oxygen transfer coefficient $K_{L,o,b} a_b$ or $K_{L,o,s} a_s$, and oxygen of $q_{o2}$ per cell unit and per time unit are consumed by a cell. In the formula (14), carbon dioxide of $q_{co2}$ per cell unit and per time unit are exhausted from a cell, and transferred in the form of gas from the liquid into the bubbles and on the liquid free surface under the volumetric carbon dioxide transfer coefficient $K_{L,co2,b} a_b$ and $K_{L,co2,s} a_s$ and finally purged out from the fermenter 1.

Each of mass transfer velocities $K_{L,i,j}$ (i=O, $CO_2$, j=b, S) described herein is given as a function of only the turbulent energy k, the turbulent energy dissipation rate $\epsilon$, and the diffusion coefficient Di (i=O, $CO_2$) that is a property value, and does not depend directly on the size of the fermenter 1, the bubble diameter, and so on. The turbulent energy k and the turbulent energy dissipation rate $\epsilon$ are calculated by the formulae (2) and (3) in the algorithm and thereby, they may be obtained at any point in any fermenter 1 only by means of computations with no experiment.

According to the present invention, the use of these volumetric mass transfer coefficients allows the fluid state in any shape of fermenter, as well as all the concentration distributions of the biomass metabolite, aerating gas, and dissolved gas to be obtained by means of computations and therefore, the shape and culture conditions of the fermenter 1 suitable for biomass culture may be known.

The results of computations executed at the processor 8 are sent to the display unit 10 and displayed. The display unit 10 may display the results of computations in the form of distribution images and/or graphs. The examples of distribution images are shown in FIGS. 4-1A to 4-1D and FIGS. 4-2A to 4-2H. FIG. 4-1A shows an example of the displayed image of a flow rate vector, FIG. 4-1B shows an example of the displayed image of the gas holdup ratio, FIG. 4-1C shows an example of the displayed image of the distribution of the turbulent energy k, FIG. 4-1D shows an example of the displayed image of the distribution of the energy dissipation rate $\epsilon$, FIG. 4-2E shows the displayed image of the distribution of the volumetric oxygen transfer coefficient Kla, FIG. 4-2F shows the displayed image of the Kolmogorov scale distribution, FIG. 4-2G shows an example of the displayed image of the oxygen concentration distribution, and FIG. 4-2H shows an example of the displayed image of the carbon dioxide concentration distribution.

Figure 5:
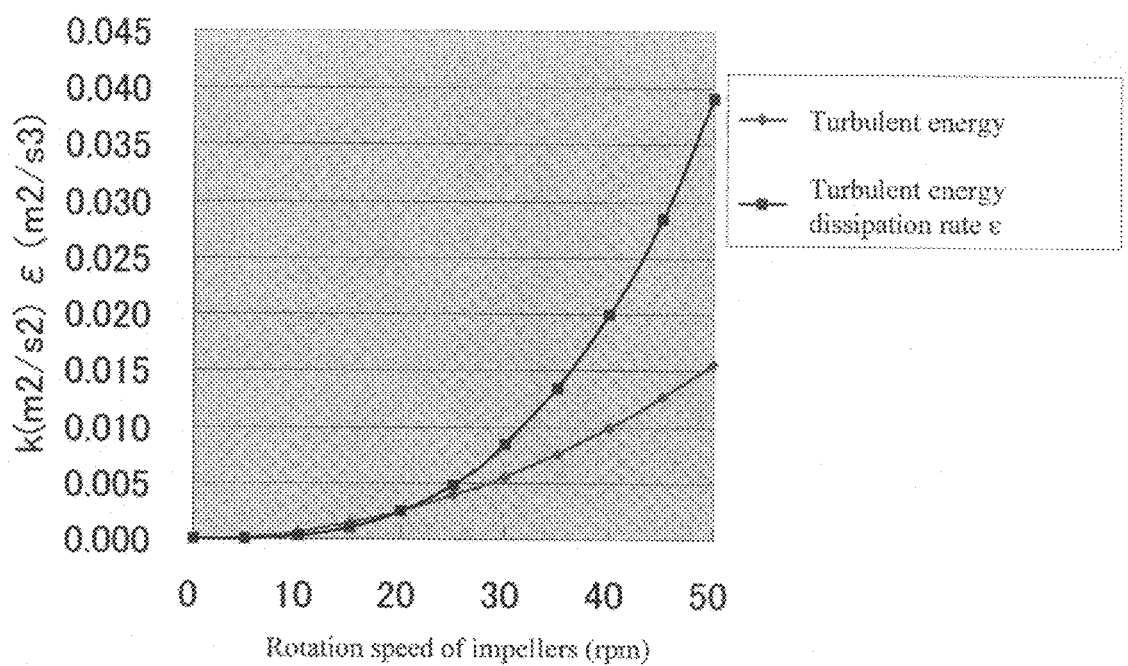
Figure 5:
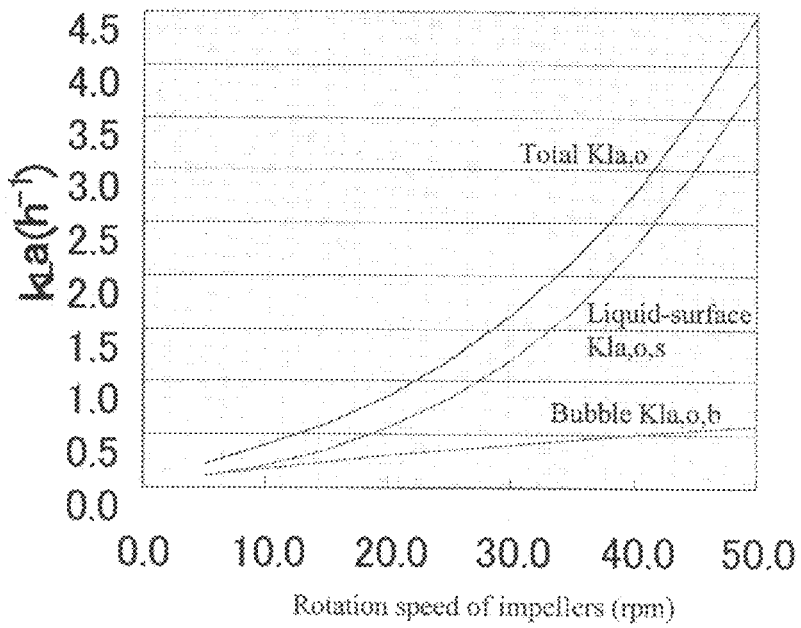

Examples of the displayed graphs are shown in FIGS. 5A and 5B. FIG. 5A shows an example of the displayed graph of the relationships between the impeller rotation speed, and turbulent energy k and the turbulent energy dissipation rate $\epsilon$. FIG. 5B shows an example of the displayed graph of the relationship between the impeller rotation speed, and the total volumetric oxygen transfer coefficient Kla, the volumetric liquid-surface oxygen transfer coefficient Kla,s, and the volumetric bubble-oxygen transfer coefficient Kla,b.

Figure 2:
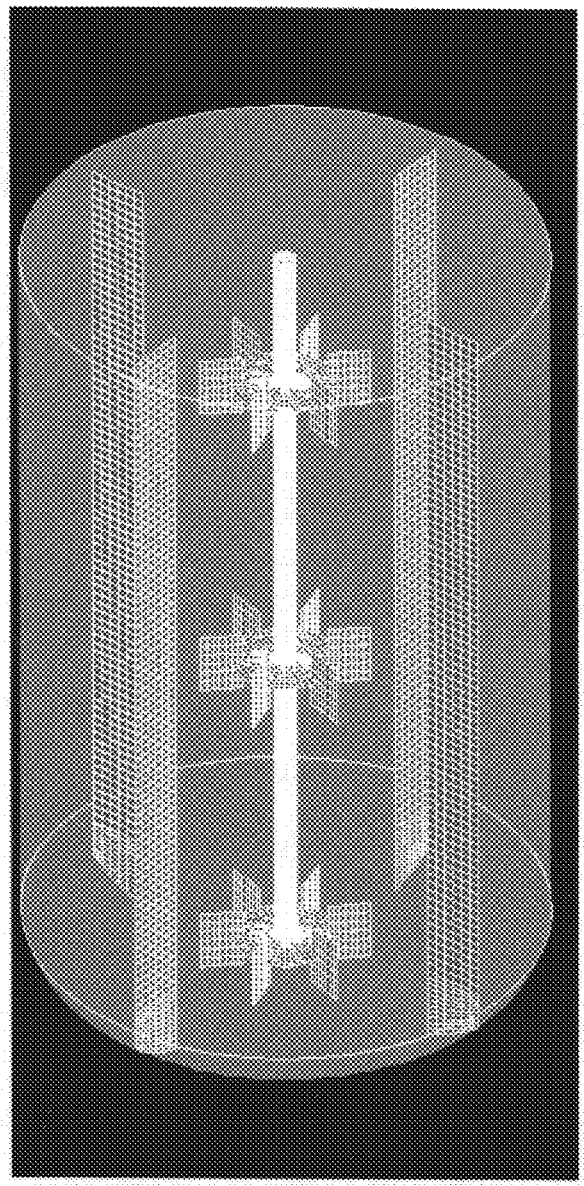
Figure 2:
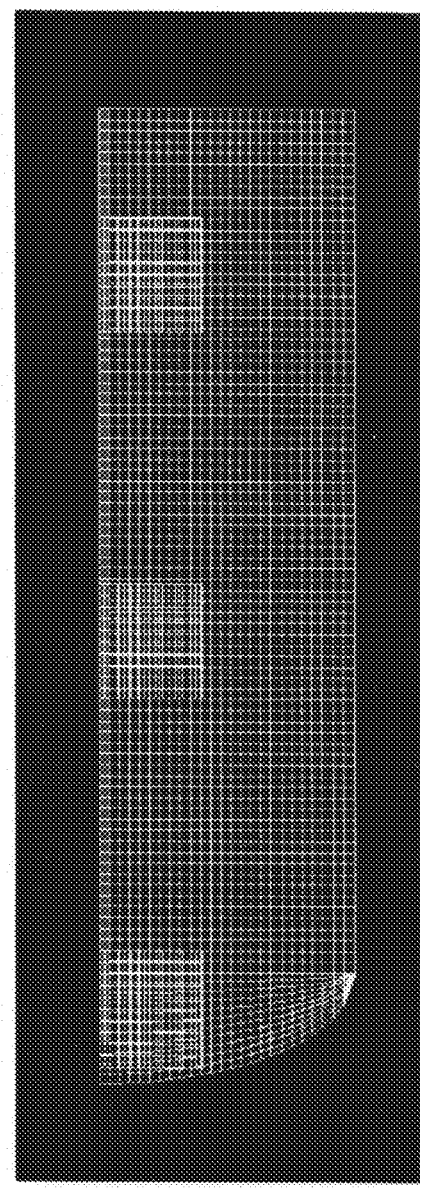

Thus, according to the control device for fermenter of the present invention, displaying the results of computation executed at the processor 8 may give quantitative information on the condition inside the fermenter 1. For example, as shown in FIGS. 4-1 and 4-2, it is clear that according to the control device for fermenter of the present invention, the turbulent energy k and the turbulent energy dissipation rate $\epsilon$ take relatively larger values around the impellers and the volumetric oxygen transfer coefficient $K_{L,o,b}a_b$ also takes a larger value as a function of these factors around the impellers. As known from FIG. 5A, as the impeller rotation speed increases, the flow rate in the fermenter becomes higher and k and $\epsilon$ increase accordingly, while the turbulent energy k increases in proportion to the square value for the rotation speed and the turbulent energy dissipation rate $\epsilon$ increases in proportion to the cubic value for the rotation speed. As shown in FIG. 5B, regarding the volumetric oxygen transfer coefficient, the dependency of $K_{L,o,b}a_b$ for bubbles and $K_{L,o,s}a_s$ for the liquid surface on the rotation speed is different. This is because the dependency of average k and $\epsilon$ values in the fermenter 1 on the rotation speed is different from the dependency of k and $\epsilon$ values in the vicinity of the liquid free surface on the rotation speed.

According to the control device for fermenter of the present invention, it is preferable that the differential equations describing the variations of the medium components over time in the aforementioned formulae (8) to (12) are modified to the differential equations suitable for different culture conditions. This means that it is preferable that the variations of the medium components over time depend on the cell line being cultured and the culture environment and thereby, the experimental constants are determined so that suitable differential equations may be established.

To achieve this, the processor 8 processes time-series measured data sent from the measurement unit 4 equipped in the fermenter 1 to determine the experimental constants for the differential equations, which best reflect the time-series measured data. In this case, it is assumed that no spatial distribution is included in the experimental constants for the differential equations. The component concentrations measured in the actual fermenter 1 generally can give only information on the averages of the components in the fermenter 1 and thereby, to obtain the detail spatial distributions, fluid dynamics calculations in the aforementioned formulae (1) to (7) are requisite. Accordingly, the differential equations given herein are assumed to describe the variations in spatial average concentrations of the medium components.

Specifically, the processor 8 takes differences between the calculated values for a historical curve of component concentration, which are obtained by numerically integrating the differential equations of the medium components and the values for a historical curve measured to determine the experimental constants, for which the differences between these values take the minimum values. For example, assuming that a set of components in the aforementioned formulae (8) to (12) is Xi (I=cell density, glucose, glutamine, lactate, ammonia) and a set of experimental constants is Kj (j=1, m), a set of the differential equations may be formally represented by:

$$\frac{dx_i}{dt} = f_i(x_1, \ldots x_n, K_1 \ldots K_m) \quad \text{[Formula 21]}$$

Defining that the observed data is $Xi^{obs}$ (t) and the calculated value is $Xi^{cal}$ (t), the calculated value is obtained by:

$$x_i(t) = x_i(0) + \int_0^T f_i(x_1, \ldots x_n, K_1, \ldots K_{in}) d\tau \quad \text{[Formula 22]}$$

Taking the square value of the difference between the measured value and the calculated value and representing a function G by:

$$G(K_1 \ldots K_m) = \int_0^T \sum_{i=1}^n \left[ x_i(0) + \int_0^t f_i(x_1, \ldots, x_n, K_1, \ldots K_m) d\tau - x_i^{obs}(t) \right]^2 dt, \quad \text{[Formula 23]}$$

the function G is represented as a function of the experimental constant Kj(j=1, m). Accordingly, the model constant Kj(j=1, m), for which the function G takes the minimum value, may be obtained by the extreme-value search theory, for example, the sequential quadratic programming or conjugate gradient method. This method may be applicable provided that the differential equation has been formulated with several experimental constants included and is not affected by the actual differential equation. Alternatively, a method, by which a Kalman filter is structured, may be applied in sequentially obtaining the experimental constants. Using the experimental constants obtained in this way in executing the computations based on the aforementioned formulae (1) to (12), the results of computations approximate to the actual fermenter conditions may be obtained. This is useful in improving the accuracy of control of the fermenter.

It is preferable that in the control device for fermenter according to the present invention, the processor 8 calculates the target value for control and the drive control unit 6 generates the drive control signals based on the target value for control. The drive control signals generated at the control device for fermenter according to the present invention control the aerating unit 2, the impeller 3, and the nutrient component feed unit 5 in the fermenter 1 to establish desired conditions in the fermenter 1.

The amount of oxygen gas aerated into the fermenter 1 by controlling the aerating unit 2 is determined in the process described below.

Figure 6:
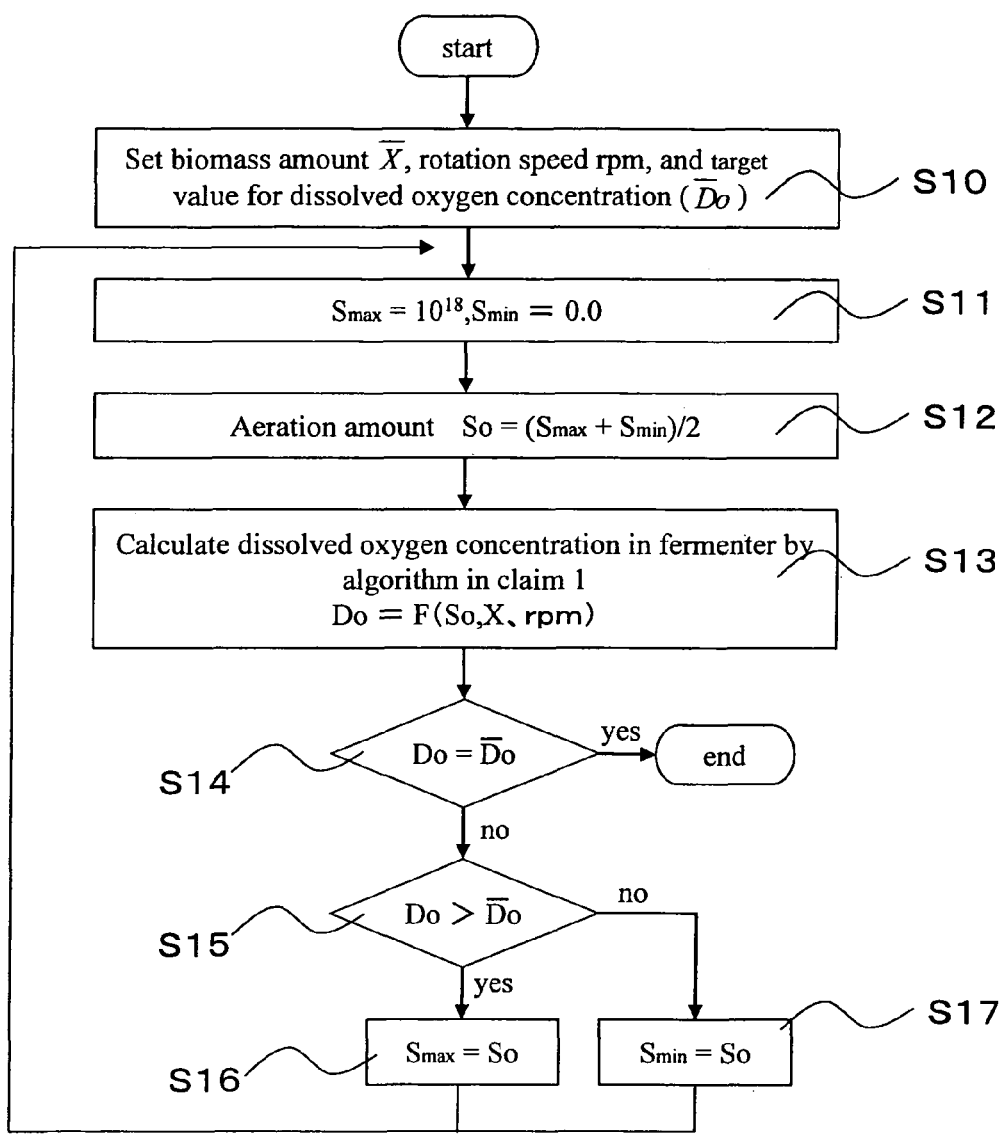
FIG. 6 is a flowchart explaining a regula falsi algorithm for obtaining the amount of aerating oxygen.

First of all, the target value for control is calculated in terms of the preset target value for a concentration of dissolved oxygen in the following manner. When the cell density Xa and agitation rotation speed rpm to increase the amount of aerating oxygen So are increased and the dissolved oxygen concentration Do that is obtained by integrating the differential equations, is a monotone increasing function of the amount of aerating oxygen So. Accordingly, using, for example, the regula falsi algorithm shown in FIG. 6, the amount of aerating oxygen So may be obtained. This means that the operator: enters the amount of biomass (X), the rotation speed (rpm) of the impellers 3, and the target value for dissolved oxygen concentration (Do) at the input unit (step 10); reads the preset the maximum amount of aerating gas $S_{max}$ (e.g., $S_{max}=10^{18}$) and specifies the minimum amount of aerating gas $S_{min}$ (e.g., $S_{min}=0$) (step 11); and sets the amount of aerating gas So (e.g., $So=(S_{max}+S_{min})/2$) (step 12). Next, the dissolved oxygen concentration Do in the fermenter 1 is calculated based on the differential equations in the formula (13) at the processor 8 (step 13). Next, The calculated dissolved oxygen concentration Do and the target value entered at the step 10 are compared (step 14) and if the calculated dissolved oxygen concentration agrees with the target value, the processing is terminated. If the calculated dissolved oxygen concentration does not agree with the target value and exceeds it (step 15), the amount of aerating gas So is re-set to $S_{max}$ (step 16) and if the calculated dissolved oxygen concentration does not exceed the target value (step 15), the amount of aerating gas So is re-set to $S_{min}$ (step 16). Finally, the step 11 and subsequent steps are repeated until the measured dissolved oxygen concentration Do agrees with the target value entered in the step 10.

For the agitation rotation speed of the impellers 3, a value suitable for the biomass to be cultured may be set. Generally, an increase in rotation speed of the impellers 3 brings an increase in turbulent energy k and turbulent energy dissipation rate $\epsilon$, which in turn, makes the volumetric oxygen transfer coefficient larger to facilitate dissolution of the oxygen gas into the culture medium. Accordingly, for example, in culturing microorganisms, the target value for control over the agitation rotation speed may be set to the maximum rotation speed under the constraint of an agitation power.

On the other hand, in culturing mammalian cells, the target value for control over the agitation rotation speed should be determined based on two factors, namely cell death due to shear stress and accumulation of dissolved carbon dioxide. When an increase in agitation rotation speed results in the increased flow rate in the fermenter 1, some of the cells come to death due to hydrodynamic shear stress. Therefore, running the impellers 3 at too high rotation speeds is not preferable in culturing the mammalian cells. The shear rate $\gamma$ of the flow represented by;

$$\gamma = \sqrt{\sum_{i=1}\sum_{j=1}\left(\frac{\partial \bar{u}i}{\partial xj}+\frac{\partial \bar{u}j}{\partial xi}\right)^2} \qquad [\text{Formula 24}]$$

and the Kolmogorov's eddy length scale $\eta$ represented by:

$$\eta = \left(\frac{v^3}{\varepsilon}\right)^{\frac{1}{4}} \qquad [\text{Formula 25}]$$

are known to be indicators for the occurrence of cell death. If $\gamma$ exceeds a given value $\gamma_{max}$ in the flow rate field in the fermenter, it is determined that the cell death occurs. Similarly, if the Kolmogorov's eddy length scale $\eta$ is smaller than cell's size scale $\eta c$, it is determined that the cell death occurs. In the present invention, all the flow rate gradients $\partial ui/\partial xj$ and the turbulent energy dissipation rates $\epsilon$ may be numerically obtained and therefore, either value of $\gamma$ or $\eta$ may be calculated at any point in the fermenter. By reference to the value, the probability of cell death may be estimated.

Figure 7:
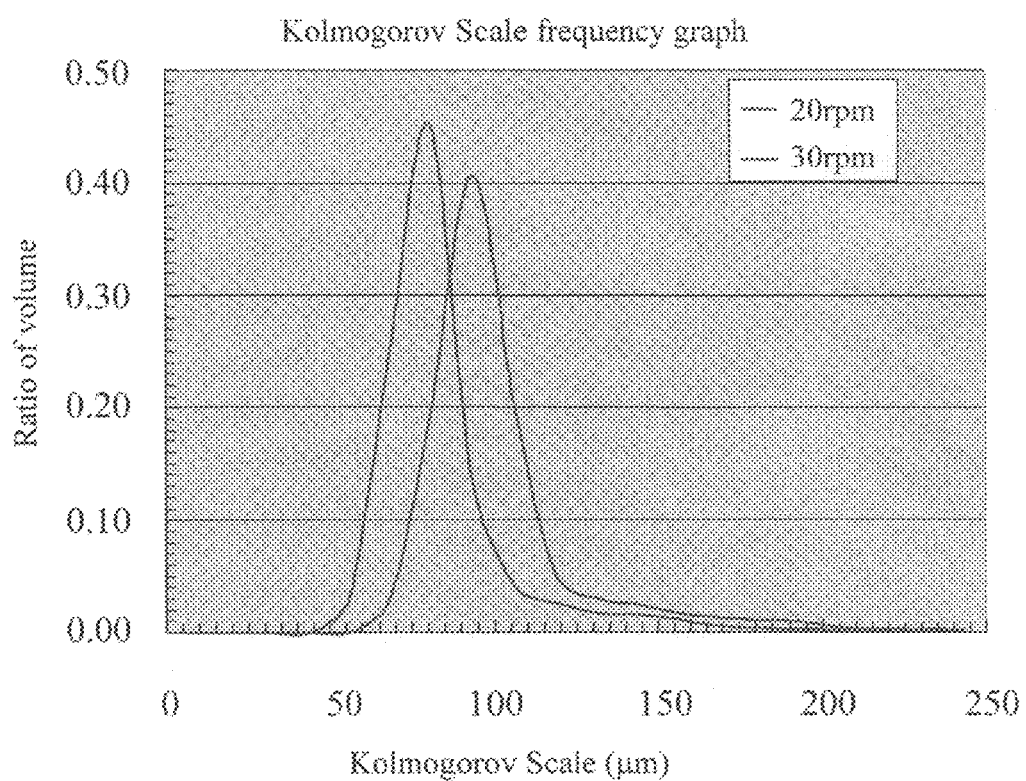
FIG. 7 is a Kolmogorov's characteristic diagram being set the rotation speed as a parameter.

The example of the displayed image of the Kolmogorov scale distribution calculated at the control device according to the present invention is shown in FIG. 4-2F. An example of the displayed graph of the Kolmogorov scale using the rotation speed as a parameter is shown in FIG. 7. With the control device according to the present invention, based on the graph shown in FIG. 7, the possibility of cell death depending on the agitation rotation speed of the impellers 3 may be estimated and the agitation rotation speed of the impellers 3 may be optimized.

Figure 8:
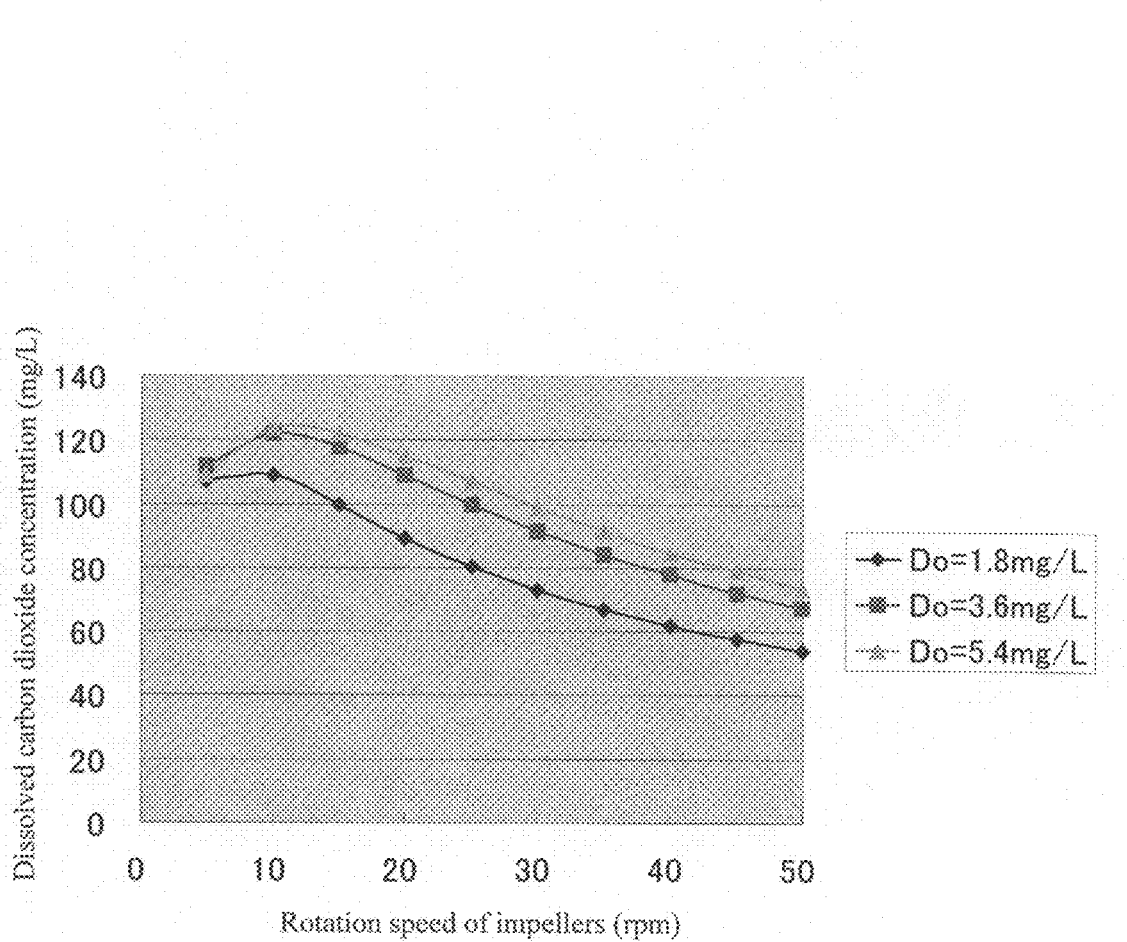
FIG. 8 is a characteristic diagram showing the dissolved carbon dioxide concentration in the fermenter calculated by evaluating the differential equations being set the rotation speed of the impellers 3 as a parameter under the condition where the cell density Xa and the dissolved oxygen concentration Do are fixed.

The agitation rotation speed of the impellers 3 affects the dissolved carbon dioxide concentration in the culture medium. If the dissolved carbon dioxide concentration in the culture medium increases, the growth rate of cells deteriorates. FIG. 8 shows the dissolved carbon dioxide concentration in the fermenter 1 obtained by solving the differential equations using the rotation speed of the impellers 3 as a parameter under the fixed conditions of cell density Xa and the dissolved oxygen concentration Do. As known from FIG. 8, when the rotation speed of the impellers 3 increases, the dissolved carbon dioxide concentration in the fermenter 1 reduces. This is because that with the increased rotation speed, the volumetric carbon dioxide transfer coefficient in the bubbles or on the liquid free surface becomes large and thereby, the speeds of transforming the dissolved carbon dioxide from the biomass transforms into the liquid phase, and purging the dissolved carbon dioxide from the fermenter 1 through the liquid free surface increase. The control device of the present invention allows the possibility of cell death depending on the agitation rotation speed of the impellers 3 to be estimated based on the graph shown in FIG. 8 and the agitation rotation speed of the impellers 3 to be optimized.

Based on the graph illustrating the Kolmogorov scale shown in FIG. 7 and the graph illustrating the dissolved carbon dioxide concentration shown in FIG. 8, the rotation speed of the impellers 3, at which the dissolved carbon dioxide concentration is minimized under such a condition that cell death does not occur, may be determined.

In addition, the processor 8 according to the present invention determines the amount of aerating gas supplied into the fermenter 1 and the target value for control over the rotation speed of the impellers 3, as well as the target value for control over nutrient supply. Under control over nutrient supply, the cells are continuously cultivated while the nutrient components consumed in the culture process are additionally supplied together with the fresh culture medium, which is called the Fed Batch method. In the Fed Batch method, the medium is continuously added with no medium extracted and thereby, the amount of liquid increases as the culture process advances. In culturing the mammalian cells, such nutrient components (the components positively involved in cell growth) as glucose, glutamine, amino acid, and serum are supplied. No medium is extracted and therefore, lactate and ammonia accumulate with no reduction in their amounts.

Focusing on the differential equations describing the variations in the medium components over time shown in the aforementioned formulae (9) to (12), the following quantitative information may be given. Decreases in glucose and glutamine reduce the cell growth rate, inhibiting an increase in cell count. Assuming that the yield of the product is proportional to the cell count, it is considered that supplying sufficient amounts of glucose and glutamine increases the yield of the product. On the other hand, focusing on the differential equations describing the variations in lactate and ammonia over time, it is considered that increases in glucose and glutamine make the lactate and ammonia concentrations higher, while increases in lactate and ammonia (the components negatively involved in cell growth) inhibit the cell growth rate. Accordingly, it is possible that at any optimal concentrations of glutamine and glucose, the cell count and the yield of the product are maximized. It is preferable that the control device according to the present invention optimally controls the supply of the medium components such as glucose and glutamine. Specifically, the processor 8 calculates the target value for control by means of dynamic programming shown in the following procedure using the differential equations in the aforementioned formulae (9) to (12). The calculated target value for control is input into the drive control unit 6. The drive control unit 6 generates the drive control signals based on the entered target value for control in order to control the supply of the medium components by the feed unit 5.

First of all, assuming that a set of cell density, lactate and ammonia (the components negatively involved in cell growth) is a state variable when the differential equations in the formulae (9) to (12) are given, $$x = (X_a, Lac, Amm) \quad \text{[Formula 26]}$$

is established. Assuming that glucose and glutamine (the components positively involved in cell growth) are supplied from the nutrient feed unit and the concentrations of glucose and glutamine are control variables, $$v = (Glc, Gln) \quad \text{[Formula 27]}$$

is established. Then, a set of differential equations in the formulae (9) to (12) may be formally described by:

$$\frac{dx}{dt} = f(x, v) \quad \text{[Formula 28]}$$

If a time axis is divided into N portions in the chronological order, the state vector at a time n+1 is obtained using the value at a time n by:

$$x_{n+1} = x_n + f(x_n, v_n)\Delta t \equiv h(x_n, v_n) \quad \text{[Formula 29]}$$

The yield of the product is considered to be proportional to the cell density and therefore, assuming that a target function is described as $$G = \int_0^T X_a \, dt \cong \sum_{n=0}^{N} g(x_n, v_n) \quad \text{[Formula 30]}$$

so as to obtain the target value for maximizing G, $v_n = v(x_n)$ [n=0, 1, ..., N]. Where, $g(x_n, v_n)$ is an integral value for a discrete minute area represented by:

$$g(x_n, v_n) = \int_{t_n}^{t_{n+1}} X_a \, dt = X_a(t_n)\Delta t + \left(\frac{dX_a}{dt}\right)_{t_n} \frac{\Delta t^2}{2} \quad \text{[Formula 31]}$$

The expression giving the maximum value for G, $$F_N(x_0) = \underset{v_0 \cdots v_N}{\text{Max}} [g(x_0, v_0) + g(x_1, v_1) + \ldots + g(x_N, v_N)] \quad \text{[Formula 32]}$$

is defined. Where, $x_0$ is an initial value for the state variable. In this case, $$\begin{aligned} F_n(x_{N-n}) &= \underset{v_{N-n}}{\text{Max}}[g(x_{N-n}, v_{N-n}) + \\ &\quad F_{n-1}(h(x_{N-n}, v_{N-n}))] \\ &= \underset{v_0}{\text{Max}}[g(x_0, v_0) + F_{N-1}(h(x_0, v_0))] \end{aligned} \quad \text{[Formula 33]}$$

are established. These relational expressions deduce a recursive expression $$F_N(x_0) = \quad \text{[Formula 34]}$$
$$\underset{v_0}{\text{Max}}\left[g(x_0, v_0) + \underset{v_1 \cdots v_N}{\text{Max}}[g(x_1, v_1) + \ldots + g(x_N, v_N)]\right]$$

at any time n with no loss of generality.

When the aforementioned recursive expression is used, an arithmetic algorithm for dynamic programming behaves as described below. It is assumed that a domain, in which the state variable X may take a value, is $x \in \Omega^3$ and a domain, in which the control variable V may take a value, is $v \in \Lambda^2$. To execute numeric calculations, the domain $\Omega^3$ for the state variable and the domain $\Lambda^2$ for the control variable are made discrete as long as the memory capacity of a computer accepts. Specifically, this means that for example, the cell density is divided into 10 domain elements from $10^6$ cells/mL to $10^7$ cells/mL in increments of $10^6$ cells/mL, the concentration of lactate is divided into 10 domain elements from 0 to 1000 mg/L in increments of 100 mg/L, and the concentration of ammonia is divided into 10 domain elements from 0 to 100 mg/L in increments of 10 mg/L. Accordingly, the domain $\Omega^3$ is divided into 1000 domain elements $\Omega^3 i$ (I=1, ..., 1000). Similarly, assuming that for example, the concentration of glucose is divided into 10 domain elements from 0 to 2000 mg/L and the concentration of glutamine is divided into 10 domain elements from 0 to 1000 mg/L, the domain $\Lambda^2$ for the control variable is divided into 100 domain elements $\Lambda^2 j$ (j=1, ..., 100).

First of all, $x \in \Omega^3_i$ for each of domain elements is obtained by:

$$F_0(x_N) = \max_{v_N \in \Lambda^2_j} [g(x_N, v_N)] \quad \text{[Formula 35]}$$

In this case, $v_N \in \Lambda^2_j$, which gives the maximum value, is different for each $x_N \in \Omega^3_i$ and thereby, $v_N$, which gives the maximum value, is $v_N = v_N(x_N)$, a function of $x_N$. This is stored in memory.

Next, for each $x_{N-1} \in \Omega^3_i$, $$F_1(x_{N-1}) = \max_{v_{N-1}} [g(x_{N-1}, v_{N-1}) + F_0(h(x_{N-1}, v_{N-1}))] \quad \text{[Formula 36]}$$

is calculated. In this case, the second term in the right side has been already determined because of the following;

$$F_0(h(x_{N-1}, v_{N-1})) = F_0(x_N) \quad \text{[Formula 37]}$$

The $v_{N-1} = v_{N-1}(x_{N-1})$, which gives the maximum value for each $x_{N-1} \in \Omega^3_i$, is stored. Subsequently, in the same manner as that mentioned above, $$F_n(x_{N-n}) = \max_{v_{N-n}} [g(x_{N-n}, v_{N-n}) + F_{n-1}(h(x_{N-n}, v_{N-n}))] \quad \text{[Formula 38]}$$

and $v_{N-n} = v_{N-n}(x_{N-n})$, which gives the maximum value, are calculated. Finally, $$F_N(x_0) = \max_{v_0} [g(x_0, v_0) + F_{N-1}(h(x_0, v_0))] \quad \text{[Formula 39]}$$

and $v_0 = v_0(x_0)$ are calculated to complete a series of computations.

$v_n = v(x_n)$ [n=0, 1, ..., N] stored in memory through the aforementioned computation process is the target control, $x_n$ [n=0, 1, ..., N] is a trajectory drawn by the state variable, and $F_N(x_0)$ is the maximum variable for the target function. In culturing cells, if a culture period is approximately 10 days and 24 hours/day are divided into 10 time elements, the time axis division number N is 100 and if a domain $\Omega^3$ for the state variable is divided into 1000 domain elements, $10^5$ array variables are required to store each $v_n = v(x_n)$ [n=1, ..., N], which is the target control in the aforementioned computation process. This requires a huge amount of memory capacity, however, the current computer sufficiently addresses this requirement of memory capacity.

At the control device according to the present invention, the target value for control used in controlling the amount of supplied medium components such as glucose and glutamine may be calculated by executing the aforementioned computation process at the processor 8. The target value for control calculated at the processor 8 is input into the drive control unit 6. At the drive control unit 6, the drive control signals are generated based on the input target value for control and the measured value read from the measurement unit 4 by for example, the PID control system. The drive control signals are output into the nutrient component feed unit 6 so as to control the amount of nutrient components supplied by the nutrient component feed unit 6. Accordingly, with the control device of the present invention, the fermenter may be driven under the condition where the biomass growth rate is maximized.

What is claimed is:

1. A control device for a fermenter comprising:
   an input device for connecting to the fermenter for entering shape data of the fermenter;
   means for generating mesh data from shape data of the fermenter, shape data of impellers of the fermenter, operating conditions of the fermenter, and initial value data;
   a measurement unit for connecting to the fermenter, in which biomass is cultured while oxygen gas is blown into a culture medium and the culture medium is stirred, for measuring nutrient components, a concentration of oxygen, a concentration of carbon dioxide, and a concentration of biomass in the culture medium;
   a processor programmed to calculate a nutrient components uptake rate, an oxygen uptake rate and a carbon dioxide exhaust rate per unit amount of biomass from the data measured by the measurement unit, as well as a volumetric mass transfer coefficient kLa from turbulent energy k calculated by a transport equation for the turbulent energy, and a turbulent energy dissipation rate e calculated by the transport equation for the turbulent energy dissipation rate, as well as a diffusion coefficient D, and programmed to calculate the concentrations of the nutrient components, dissolved oxygen, and dissolved carbon dioxide in any area in the fermenter using an algorithm to numerically integrate a transport equation that is a differential equation describing variations in medium components over time from the calculated nutrient components uptake rate, the calculated oxygen uptake rate, the calculated carbon dioxide exhaust rate, and the calculated volumetric mass transfer coefficient kLa; and
   means for displaying concentration distributions of the nutrient components, dissolved oxygen, and dissolved carbon dioxide in the fermenter based on the concentrations of the nutrient components, dissolved oxygen, and carbon dioxide in any area of the fermenter calculated by the processor.

2. The control device for fermenter according to claim 1, wherein the processor compares the calculated dissolved oxygen concentration and a preset targeted value for dissolved oxygen concentration so as to generate a control signal for controlling the amount of oxygen gas to be supplied to the fermenter.

3. The control device for fermenter according to claim 1, wherein the processor calculates a value for an indicator of biomass death so as to generate a control signal for controlling a rotation speed of the impellers of the fermenter.

4. The control device for fermenter according to claim 1, wherein the differential equation contains experimental constants and the processor calculates the experimental constants so that the data measured by the measurement unit corresponds to data on the measured value obtained by numerically integrating the differential equation by a least squares method to re-establish the differential equation.

5. The control device for fermenter according to claim 1, wherein the input device enters measured data on biomass concentration, components having positive effects on biomass concentration, and components having negative effects on cell growth, wherein when a formula calculating an yield of a product to be harvested is a target function, a concentration of the component having negative effects on cell density and cell growth is a state variable, and a concentration of the component having positive effects on cell growth is a control variable, the processor divides variance ranges of the state variable and the control variable into a finite number of partial regions, respectively, so as to generate control signals for time series supply of the components having positive effects on cell growth such that the target function can be maximized using dynamic programming.

6. A fermentation unit comprising:
a fermenter, in which biomass is cultured while oxygen gas is blown into a culture medium and the culture medium is stirred;
a measurement unit connected to the fermenter for measuring nutrient components, a concentration of oxygen, a concentration of carbon dioxide, and a concentration of biomass in the culture medium in the fermenter;
an input device connected to the fermenter for entering shape data on the fermenter, and for entering measured data regarding at least the nutrient components, concentration of oxygen, concentration of carbon dioxide, and concentration of biomass in the culture medium in the fermenter, which are measured by the measurement unit;
a processor programmed to calculate a nutrient components uptake rate, an oxygen uptake rate and a carbon dioxide exhaust rate per unit amount of biomass from the data measured by the measurement unit, as well as volumetric mass transfer coefficient kLa from turbulent energy k and a turbulent energy dissipation rate e, both of which are calculated by a transport equation, as well as a diffusion coefficient D, and programmed to calculate the concentrations of the nutrient components, dissolved oxygen, and dissolved carbon dioxide in any area in the fermenter using an algorithm to numerically integrate a differential equation describing variations in medium components over time from the calculated nutrient components uptake rate, the calculated oxygen uptake rate, the calculated carbon dioxide exhaust rate, and the calculated volumetric mass transfer coefficient kLa, wherein the processor calculates mesh data for the fermenter based on the shape data entered by the input device; and
a display means for displaying concentration distributions of the nutrient components, dissolved oxygen, and dissolved carbon dioxide in the fermenter based on the concentrations of the nutrient components, dissolved oxygen, and carbon dioxide in any area of the fermenter calculated by the processor.

7. The fermentation unit according to claim 6, further comprising:
an oxygen gas feed unit for feeding an oxygen gas into the fermenter based on a control signal,
wherein the control signal is calculated by comparing the dissolved oxygen concentration that are calculated by the processor and a preset targeted value for dissolved oxygen concentration at the processor and the control signal controls the amount of oxygen gas to be supplied into the fermenter.

8. The fermentation unit according to claim 6, wherein, the value for the indicator of biomass death is calculated at the processor and the rotation speed of the impellers in the fermenter is controlled based on the control signal generated at the processor.

9. The fermentation unit according to claim 6, wherein the differential equation contains experimental constants and the processor calculates the experimental constants so that the data entered at the measurement unit corresponds to data on the measured value obtained by numerically integrating the differential equation by a least squares method to reestablish the differential equation.

10. The fermentation unit according to claim 6, further comprising:
a feed unit for supplying the components having positive effects on cell growth in the fermenter,
wherein the measurement unit measures a data on biomass concentration, components having positive effects on cell growth, and components having negative effects on cell growth, wherein when a formula calculating a yield of a product to be harvested is a target function, a concentration of the component having negative effects on cell density and cell growth is a state variable, and a concentration of the component having positive effects on cell growth is a control variable, the processor divides variance ranges of the state variable and the control variable into a finite number of partial regions, respectively, so as to generate control signals for time series supply of the components having positive effects on cell growth such that the target function can be maximized using dynamic programming, and wherein the feed unit supplies the components having positive effects on cell growth in the fermenter based on the control signals for time series supply.

11. The fermentation unit according to claim 1, wherein the control device sets a target value for rotation speed of the impellers of the fermenter based on a cell density and a dissolved oxygen concentration calculated by the processor, so that a dissolved carbon dioxide concentration is lower than a set value.

12. The fermentation tank according to claim 6, wherein the control device sets a target value for rotation speed of impellers of the fermenter based on a cell density and a dissolved oxygen concentration calculated by the processor, so that a dissolved carbon dioxide concentration is lower than a set value.

* * * * *